(12) United States Patent
Matsushima et al.

(10) Patent No.: US 8,088,314 B2
(45) Date of Patent: Jan. 3, 2012

(54) PROCESS FOR PRODUCING SURFACE-TREATED INTRAOCULAR LENS AND INTRAOCULAR LENS CAPABLE OF INHIBITING SECONDARY CATARACT

(75) Inventors: Hiroyuki Matsushima, Utsunomiya (JP); Hidetoshi Iwamoto, Fukaya (JP)

(73) Assignee: Hoya Corporation, Tokyo (JP)

( * ) Notice: Subject to any disclaimer, the term of this patent is extended or adjusted under 35 U.S.C. 154(b) by 548 days.

(21) Appl. No.: 11/666,010

(22) PCT Filed: Nov. 8, 2005

(86) PCT No.: PCT/JP2005/020783
§ 371 (c)(1),
(2), (4) Date: Nov. 1, 2007

(87) PCT Pub. No.: WO2006/051930
PCT Pub. Date: May 18, 2006

(65) Prior Publication Data
US 2009/0024115 A1 Jan. 22, 2009

(30) Foreign Application Priority Data
Nov. 10, 2004 (JP) ................................. 2004-326777

(51) Int. Cl.
*A61F 2/16* (2006.01)
(52) U.S. Cl. ...................... 264/1.36; 623/6.16; 623/6.56
(58) Field of Classification Search ........ 623/6.11–6.64; 430/4; 427/2.27; 522/49; 264/1.1
See application file for complete search history.

(56) References Cited

U.S. PATENT DOCUMENTS

| 6,113,817 | A * | 9/2000 | Herbrechtsmeier et al. | 264/1.36 |
| 6,749,632 | B2 * | 6/2004 | Sandstedt et al. | 623/6.22 |
| 2002/0016639 | A1 * | 2/2002 | Smith et al. | 700/9 |

FOREIGN PATENT DOCUMENTS

| EP | 0 811 393 A1 | 12/1997 |
| EP | 1 043 365 A1 | 10/2000 |
| JP | 02-257962 | 10/1990 |
| JP | 7-313538 | 12/1995 |
| JP | 8-311045 | 11/1996 |
| JP | 9-291040 | 11/1997 |
| JP | 10-24097 | 1/1998 |
| JP | 10-195324 | 7/1998 |
| JP | 2001-252346 | 9/2001 |
| JP | 2002-511315 | 4/2002 |
| JP | 2002-325829 | 11/2002 |
| JP | 586923 | 5/2004 |
| JP | 2004-275386 | 10/2007 |
| WO | WO 99/52570 | 10/1999 |

OTHER PUBLICATIONS

Nishi, Okihiro, et al, "Secondary Cataract Inhibiting Effect of Intraocular Lens", Summary of the 15th Europe Intraocular Lens Society Conference, 1997, English abstract.
Babizhayev, M.A., et al, "Tinting effect of ultraviolet radiation on intraocular lenses of polymethyl methacrylate", Bio-Med Mater Eng., 1994, vol. 4, No. 1, pp. 1-16, p. 2, line 26 to p. 4, line 2.

* cited by examiner

*Primary Examiner* — David H Willse
*Assistant Examiner* — Tiffany Shipmon
(74) *Attorney, Agent, or Firm* — Nixon & Vanderhye P.C.

(57) ABSTRACT

Provided are a process for producing an intraocular lens capable of inhibiting secondary cataract that may occur after the insertion of an intraocular lens and a secondary-cataract-inhibiting intraocular lens obtained by the above process, and the process is for producing a surface-treated intraocular lens, which comprises irradiating the surface of an intraocular lens with active light that works to decompose oxygen molecules to generate ozone and that also works to decompose the ozone to generate active oxygen, in the presence of oxygen, and the lens is a secondary-cataract-inhibiting intraocular lens obtained by the above process.

4 Claims, No Drawings

PROCESS FOR PRODUCING SURFACE-TREATED INTRAOCULAR LENS AND INTRAOCULAR LENS CAPABLE OF INHIBITING SECONDARY CATARACT

TECHNICAL FIELD

The present invention relates to a process for producing a surface-treated intraocular lens and an intraocular lens capable of inhibiting secondary cataract. More specifically, it relates to a process for producing a surface-treated intraocular lens that is to be inserted after the extraction of a lens having suffered from cataract and that is capable of inhibiting secondary cataract which may occur after surgery, and a secondary-cataract-inhibiting intraocular lens consisting of a surface-treated intraocular lens obtained by the above process.

TECHNICAL BACKGROUND

In recent years, with an increase in the population of the aged people, the number of aged patients having senile cataract has noticeably increased. The cataract is a disease in which a crystalline lens is opacified, and it induces a decrease in the vision depending upon the degree, region and site of the opacification and may sometimes deprive a patient of his or her eyesight. When a patient with cataract is treated, the opaque crystalline lens and cortex are removed and the vision is corrected with an ophthalmic lens or a contact lens, or an intraocular lens is inserted. It is a generally practiced method at present to remove the crystalline lens and then fix an intraocular lens in the capsule.

In the above method, however, remaining crystalline lens epithelial cells migrate into the posterior lens capsule and proliferate to generate opacification in the posterior capsule region, and the opacification may spread over the optic portion of the intraocular lens and may cause secondary cataract. For treating this secondary cataract after the insertion of an intraocular lens, there is employed a method in which the opacified portion is removed by irradiation with an ND:YAG laser beam. However, this method has defects that the apparatus therefor is expensive and that the fundus examination, photocoagulation and vitreous body operation are hampered (for example, see NISHI Okihiro, et al., "Secondary Cataract Inhibiting Effect of Intraocular Lens", Summary of the 15th Europe Intraocular Lens Society Conference, 1997).

As other method, there are known a method of treating and preventing secondary cataract by using a medicine (for example, see JP-A-9-291040), a method of forming an intraocular lens whose circumferential portion has sharp edges to inhibit the secondary cataract (for example, see the above Summary of the 15th Europe Intraocular Lens Society Conference) and a method of coating that portion of an intraocular lens which corresponds to the posterior capsule portion with a biocompatible material having a specific composition (for example, see Japanese Translation Version No. 2002-511315 of PCT Application).

The above methods have an effect on the inhibition of secondary cataract to some extent. However, they have problems that it is required to organize a new combination of an intraocular lens and a medicine and that additional precision-processing is required for finishing a sharp circumferential portion. It has been therefore desired to develop a process for further simply producing an intraocular lens capable of inhibiting secondary cataract.

DISCLOSURE OF THE INVENTION

Under the circumstances, it is an object of the present invention to provide a process for producing an intraocular lens capable of inhibiting secondary cataract that may occur after the insertion of an intraocular lens, and a secondary-cataract-inhibiting intraocular lens consisting of an intraocular lens obtained by the above process.

The present inventors have made diligent studies for methods for inhibiting secondary cataract. As a result, it has been found that the adsorpability of fibronectin as an adhesive protein to an intraocular lens is improved so that an excellent secondary-cataract-inhibiting effect is exhibited when an intraocular lens is surface-modified by irradiating the surface of the intraocular lens with active light that works to decompose oxygen molecules to generate ozone and that also works to decompose the ozone to generate active oxygen, in the presence of oxygen. On the basis of this finding, the present invention has been completed.

That is, the present invention provides;

(1) a process for producing a surface-treated intraocular lens, which comprises irradiating the surface of an intraocular lens with active light that works to decompose oxygen molecules to generate ozone and that also works to decompose the ozone to generate active oxygen, in the presence of oxygen, (2) a process of the above (1), wherein the active light is light having two peaks in a wavelength region of 150 to 300 nm, (3) a process of the above (2), wherein the active light is light having emission peaks at a wavelength region of 185±5 nm and a wavelength region of 254±5 nm, (4) a process of any one of the above (1) to (3), wherein the intraocular lens is a soft lens, (5) a process of the above (4), wherein the soft lens is formed of a soft acrylic material, (6) a process of any one of the above (1) to (3), wherein the intraocular lens has an optic portion formed of a hard lens, and (7) an intraocular lens capable of inhibiting secondary cataract, which is a surface-treated intraocular lens produced by the process recited in any one of the above (1) to (6).

According to the present invention, there can be provided a process for producing a surface-treated intraocular lens that is to be inserted after the extraction of a lens suffering from cataract and that is capable of inhibiting secondary cataract that may occur after the surgery for the insertion, and an intraocular lens capable of inhibiting secondary cataract, which is a surface-treated intraocular lens obtained by the above process.

PREFERRED EMBODIMENTS OF THE INVENTION

In the process for producing a surface-treated intraocular lens, provided by the present invention, an intraocular lens is irradiated with active light that works to decompose oxygen molecules to generate ozone and that also works to decompose the ozone to generate active oxygen, in the presence of oxygen. It is considered that active oxygen species react with a lens surface by the above irradiation whereby the lens is surface-treated.

In the present invention, the active light to be used for the irradiation is preferably light that has two peaks in a wavelength region of 150 to 300 nm and that works to decompose oxygen molecules to generate ozone and also works to decompose the ozone to generate active oxygen species. In particular, the active light is, for example, light having emission peaks at a wavelength region of 185±5 nm and a wavelength region of 254±5 nm. This active light can be generated, for example, by means of a low-pressure mercury lamp.

In the present invention, the irradiation with the above active light is carried out in the presence of oxygen for generating active oxygen species. As the above oxygen, oxygen gas can be used, or an oxygen-containing gas such as air can be used.

It is considered that when the irradiation is carried out with light having emission peaks at a wavelength region of 185±5 nm and a wavelength region of 254±5 nm, light in a wavelength region of 185±5 nm decomposes oxygen molecules first to generate ozone and then light in a wavelength region of 254±5 nm decomposes the above ozone to generate active oxygen species having high energy.

While conditions for the irradiation with active light are not specially limited, they are selected as required by taking account of a material forming the optic portion of the intraocular lens. When the irradiation intensity of the active light is high, the irradiation can be finished for a short period of time. Since, however, the irradiation may induce the deterioration of the lens, caution is required. Further, since some materials are structurally easily decomposable, it is desirable to make studies in advance. Further, when the irradiation time period is long, coloring is sometimes caused, so that this point requires caution. Desirably, the intraocular lens is washed before it is irradiated.

When the optic portion of the intraocular lens is surface-treated in the above manner, the capability thereof for adhesion of fibronectin as an adhesive protein is improved, and as a result the secondary cataract that may occur after the surgery can be inhibited.

Regarding this point, Reijo J. Linnola, et al suggest that fibronectin plays an important role in adhesion of the optic portion of an intraocular lens to a capsule (J. Cataract Refract Surg. 2000; 26: 1792-1806) and that a lens to which fibronectin has high capability of adhesion will be effective for inhibiting secondary cataract.

In the present invention, the intraocular lens to be surface-treated is not specially limited, and there can be used both a soft lens whose optic portion is foldable and a hard lens which is non-foldable. The above soft lens and hard lens are not specially limited, either, while an acrylic material is preferred.

The acrylic material to be used for the above soft lens can be, for example, a polymer obtained from at least two monomers selected from 2-phenylethyl methacrylate, 3-phenylpropyl methacrylate, 2-phenoxyethyl methacrylate, 2-phenylethyl acrylate, 3-phenylpropyl acrylate, 2-phenoxyethyl acrylate, ethyl acrylate, n-propyl acrylate, isobutyl acrylate, isoamyl acrylate, hexyl acrylate, 2-hydroxy methacrylate and n-vinylpyrrolidone and at least one member of crosslinking agent selected from ethylene glycol di(meth)acrylate, diethylene glycol di(meth)acrylate, triethylene glycol di(meth)acrylate, 1,4-butanediol di(meth)acrylate and 1,6-hexanediol di(meth)acrylate.

The acrylic material to be used for the hard lens can be, for example, a polymer obtained from at least one member selected from methyl methacrylate, ethyl methacrylate, and the like.

The intraocular lens for use in the present invention is particularly preferably a soft lens formed of a soft acrylic material.

The amount of the crosslinking agent based on the total monomer amount is preferably 0.3 to 5% by weight, particularly preferably 0.5 to 4% by weight. When the amount of the crosslinking agent is less than 0.3% by weight, the effect based on introduction thereof is not fully exhibited. When it exceeds 5% by weight, the number of crosslinking points increases to make a lens fragile and to cause the mechanical strength to decrease. For the polymerization, heat, light, electron beam, etc., may be used. The amount of a polymerization initiator based on the total monomer amount is preferably 0.1 to 2% by weight, particularly preferably 0.2 to 1% by weight.

The form of the intraocular lens is not specially limited, and examples thereof include a one-piece intraocular lens whose optic portion and haptic portions are integrated and a three-piece intraocular lens whose haptic portions are formed of polypropylene, P-MMA or the like.

Further, the above monomers may contain a monomer having ultraviolet absorption capability, such as 2-(2-hydroxy-3-tert-butyl-5-methylphenyl)-5-(2-methacryloxyethyl)benzotriazole or the like. The amount of this monomer based on the total amount of the above monomers is preferably 0.1 to 4% by weight, particularly preferably 0.5 to 2% by weight. For correcting cyanopsia, further, the above monomers may contain a yellow reactive monomer having a yellow chromophore such as 4-(5-hydroxy-3-methyl-1-phenyl-4-pyrazolylmethyl)-3-methacrylamino-1-phenyl-2-pyrazolin-5-one or the like.

In the present invention, the process for producing an intraocular lens whose surface is to be treated is not specially limited and can be selected from conventionally known processes.

Specifically, there can be employed (1) a process for producing an intraocular lens, in which a plastic disk having a concave portion, prepared from a material for forming haptic portions, is provided, the monomers for forming an optic portion are poured into the above concave portion and polymerized, and then the resultant product is cut to a predetermined form and polished, (2) a process for producing an intraocular lens, in which an acrylic monomer for forming haptic portions is filled around the circumferential portion of a rod-like plastic member formed of a material for an optic portion and polymerized and then a polymerization product is cut to a predetermined form and polished or (3) a process in which monomers are poured into a resin mold having a space having the form of an intraocular lens and an optic portion and haptic portions are formed from the one and same material.

In the above process (1), the material for the plastic disk having a concave portion, prepared from a material for forming haptic portions, is selected from polyalkyl methacrylate, a fluorine resin (polyvinylidene fluoride), a polyimide resin or the like.

In the above process (2), the acrylic monomer for forming haptic portions includes monomers for forming the polyalkyl methacrylates, which are described as examples of materials for constituting the plastic disk having a concave portion in the above process (1).

In the above process (3), further, the monomer for forming an optic portion and haptic portions includes the monomers described as examples of monomers for obtaining the acrylic materials for the above soft lens and hard lens.

EXAMPLES

The present invention will be explained in detail below with reference to Examples, while the present invention shall not be limited by these Examples.

A fibronectin adhesion test showing adhesion of cells to each lens obtained in Examples and a secondary cataract inhibition test using a rabbit eye were carried out as follows.

(1) Fibronectin Adhesion Test

Two mg of fibronectin (HFN; supplied by Haematologic Technologies Inc.) was dissolved in 5 ml of pure water, and OPEGUARD MA (supplied by Senju Pharmaceutical Co., Ltd.) was added up to 40 ml as a total, to prepare a 50 μg/ml solution. On the other hand, a test lens was placed in a serum tube, 2 ml of the fibronectin solution was added and the tube was tightly stoppered and shaken with a bioshaker (TAITEC, BR-3000LF) at 37° C. for 24 hours.

After completion of the shaking, the sample was taken out, a liquid on the lens surface was wiped off with Kim Wipe and the lens was placed in a glass test tube for amino acid analysis.

In the amino acid analysis, 200 μl of 6 mol/L hydrochloric acid was added to the glass test tube with the test lens in it, the glass test tube was sealed under reduced pressure, and hydrolysis was carried out at 110° C. for 22 hours. After the hydrolysis, a reaction mixture was dried to solidness under reduced pressure, and a residue was dissolved in 100 μm of pure water. The resultant solution was filtered with a 0.22 μm filter, 50 μl of the resultant filtrate was subjected to amino acid analysis (Hitachi L-8500 Amino Acid Analyzer/ninhydrin color development method).

(2) Secondary Cataract Inhibition Test Using Rabbit Eye
[Operation of Lens Implantation in Rabbit Eye]

A white rabbit (about 2 kg) of 8 weeks' age which was had been mydriatic with an ophthalmic drug (trade name: MYDRIN-P, supplied by Santen Pharmaceutical Co., Ltd.) before surgery was subjected to general anesthesia and subjected to the treatment by phacoemulsification and aspiration (PEA) and a lens was inserted through a 4.0 mm corneal incision.

[Preparation of Tissue Sample]

Two weeks after the surgery, the rabbit was euthanized, and an eyeball was extracted and immobilized with 10 wt % formalin. After dehydration, a paraffin section was prepared, subjected to the treatment of paraffin removal and then stained with hematoxylin and eosin. The tissue section was divided into an intraocular lens central portion and a circumferential portion and observed through a biomicroscope ("BX-51" supplied by Olympus Corporation).

Example 1

98 Parts by weight of MMA (methyl methacrylate), 2 parts by weight of EDMA (ethylene glycol dimethacrylate), 0.3 part by weight of AIBN (azoisobutyronitrile) and a blue reactive dye (0.06% based on the total monomer weight) were placed in a beaker and fully stirred to form a monomer solution. A tube having an internal diameter of 18 mm and a length of 500 mm, formed of polyethylene, was provided in advance and was filled with this monomer solution, and the tube was stoppered. The monomers were polymerized in a water bath at 40° C. for 48 hours and further in a drying chamber at 90° C. for 12 hours to give a rod-shaped PMMA (polymethyl methacrylate) polymer product. Then, a hole having a radius of 3 mm from the center of the rod-shaped polymer product was made in the above rod-shaped polymer product and the rod-shaped polymer product was cut to a thickness of 5 mm to give a doughnut-like holed disk.

The above disk with the hole was placed in a die formed of polypropylene, and the hole was filled with a monomer solution for forming an optic portion [52 parts by weight of PEMA (2-phenylethyl methacrylate), 42 parts by weight of n-BA (n-butyl acrylate), 6 parts by weight of BRM (perfluorooctylethyloxypropylene methacrylate), 2 parts by weight of EDMA, 0.3 part by weight of AIBN and 1.50% (based on the total weight of the monomers) of T-150], followed by polymerization at predetermined temperatures. That is, the monomer mixture was temperature-increased from room temperature to 60° C. and maintained at 60° C. for 12 hours. Then, it was temperature-increased to 80° C. over 60 minutes and maintained for 2 hours. Further, it was temperature-increased to 100° C. over 60 minutes, maintained at 6 hours and the temperature-decreased to room temperature to give a disk whose central portion was formed of the soft acrylic resin and whose circumferential portion was formed of the blue PMMA.

The above disk was cut with a milling machine and ground and polished by a general method to give a one-piece lens which had blue PMMA haptic portions and had an optic portion of 6 mm in diameter, which was formed of the soft acrylic resin (total length: 13 mm) (see footnotes to Table 1 for the above abbreviations).

Then, the above lens was placed 10 mm below a low-mercury lamp in the chamber of "Photo Surface Processor (PL16-110)" supplied by SEN LIGHTS CORPORATION, and its front and reverse surfaces were irradiated with active light having emission peaks at or around 185 nm and 254 nm in the presence of air for 120 seconds. After the irradiation, the thus-obtained lens was sterilized with EOG (ethylene oxide gas) and subjected to the fibronectin adhesion test and the secondary cataract inhibition test using a rabbit.

As a result of the fibronectin adhesion test, it was found that the fibronectin adhesion amount was 0.75 μg/piece.

Further, as a result of the secondary cataract inhibition test using a rabbit, it was observed that crystalline lens epithelial cells proliferated in a circumferential portion of the intraocular lens. However, in the central portion of the intraocular lens, it was found that crystalline lens epithelial cells proliferated to a slight degree but they were of a single layer, so that the occurrence of secondary cataract was clearly inhibited.

A biomicroscopic photograph of the epithelial cells adhering to the central portion of the intraocular lens showed that the adhering epithelial cells had a thickness of 13.0 μm.

Table 2 shows these results.

Example 2

Example 1 was repeated except that a one-piece lens formed of the soft acrylic resin was irradiated with active light for 180 seconds.

As a result of the fibronectin adhesion test, it was found that the fibronectin adhesion amount was 0.98 μg/piece.

Further, as a result of the secondary cataract inhibition test using a rabbit, it was observed that crystalline lens epithelial cells proliferated in a circumferential portion of the intraocular lens. However, in the central portion of the intraocular lens, it was found that crystalline lens epithelial cells proliferated to a slight degree but they were of a single layer, so that the occurrence of secondary cataract was clearly inhibited.

A biomicroscopic photograph of the epithelial cells adhering to the central portion of the intraocular lens showed that the adhering epithelial cells had a thickness of 11.0 μm.

Table 2 shows these results.

Example 3

Example 1 was repeated except that Example 3 used materials and their amounts shown in Table 1 and that a one-piece lens having haptic portions (blue) and an optic portion (yellow) formed of a yellow soft acrylic resin was prepared in the same manner as in Example 1.

As a result of the fibronectin adhesion test, it was found that the fibronectin adhesion amount was 0.82 μg/piece.

Further, as a result of the secondary cataract inhibition test using a rabbit, it was observed that crystalline lens epithelial cells proliferated in a circumferential portion of the intraocular lens. However, in the central portion of the intraocular lens, it was found that crystalline lens epithelial cells proliferated to a slight degree but they were of a single layer, so that the occurrence of secondary cataract was clearly inhibited.

Table 2 shows these results.

Comparative Example 1

Example 1 was repeated except that the irradiation of a one-piece lens formed of a soft acrylic resin with active light was not carried out.

As a result of the fibronectin adhesion test, it was found that the fibronectin adhesion amount was 0.30 μg/piece.

Further, as a result of the secondary cataract inhibition test using a rabbit, it was observed that crystalline lens epithelial cells proliferated in a circumferential portion of the intraocular lens, and in the central portion of the intraocular lens, crystalline lens epithelial cells that proliferated spread between the intraocular lens and a posterior capsule and formed multiple layers and high-degree secondary cataract occurred.

A biomicroscopic photograph of the epithelial cells adhering to the central portion of the intraocular lens showed that the adhering epithelial cells had a thickness of 55.3 μm.

Table 2 shows these results.

Comparative Example 2

A one-piece lens formed of a yellow soft acrylic resin, prepared in the same manner as in Example 3, was placed and kept on in air in a box with a sterilization lamp having a peak at 253.7 nm (supplied by Toshiba Corporation) for 15 minutes to carry out sterilization, followed by EOG sterilization. The lens was subjected to the fibronectin adhesion test and the secondary cataract inhibition test using a rabbit.

As a result of the fibronectin adhesion test, it was found that the fibronectin adhesion amount was 0.32 μg/piece.

Further, as a result of the secondary cataract inhibition test using a rabbit, it was observed that crystalline lens epithelial cells proliferated in a circumferential portion of the intraocular lens, and in the central portion of the intraocular lens, crystalline lens epithelial cells that proliferated spread between the intraocular lens and a posterior capsule and formed multiple layers and high-degree secondary cataract occurred.

TABLE 1

| | | Ex. 1, Ex. 2, CEx. 1 | Ex. 3 CEx. 2 |
|---|---|---|---|
| Composition for haptic portions (*) | MMA | 98 | 98 |
| | EDMA | 2 | 2 |
| | AIBN | 0.3 | 0.3 |
| | AQ-1 | 0.06% | 0.06% |
| Composition for optic portion (*) | PEMA | 52 | 52 |
| | n-BA | 42 | 42 |
| | BRM | 6 | 6 |
| | EDMA | 2 | 2 |
| | AIBN | 0.3 | 0.3 |

TABLE 1-continued

| | Ex. 1, Ex. 2, CEx. 1 | Ex. 3 CEx. 2 |
|---|---|---|
| T-150 | 1.50% | 1.00% |
| HMPO | — | 0.02% |

Ex. = Example, CEx. = Comparative Example
*Unit other than % is "part by weight".
% was calculated based on the total monomer amount.
(Notes)
MMA: Methyl methacrylate
EDMA: Ethylene glycol dimethacrylate
PEMA: 2-Phenylethyl methacrylate
BRM: Perfluorooxtylethyloxypropylene methacrylate
n-BA: n-Butyl acrylate
AIBN: 2,2'-azobis(isobutyronitrile)
T-150: 1-(2-hydroxy-3-tert-butyl-5-methylphenyl)-5-(2-methacryloxyethyl)benzotriazole
AQ-1: 1-Anilino-4-(4-vinylbenzyl)aminoanthraquinone
HMPO: 4-(5-Hydroxy-3-methyl-1-phenyl-4-pyrazolylmethylene)-3-methacrylamino-1-phenyl-2-pyrazolin-5-one

TABLE 2

| | Adhesion amount of fibronectin (μg/piece) | Thickness of epithelial cells (μm) |
|---|---|---|
| Example 1 | 0.75 | 13.0 |
| Example 2 | 0.98 | 11.0 |
| Example 3 | 0.82 | — |
| Comparative Example 1 | 0.30 | 55.3 |
| Comparative Example 2 | 0.32 | — |

INDUSTRIAL UTILITY

According to the present invention, there can be provided an intraocular lens that can inhibit secondary cataract by simple surface treatment in which the intraocular lens is irradiated with active light having a specific function in the presence of oxygen.

The invention claimed is:

1. A process for producing a surface-treated intraocular lens that inhibits secondary cataract, which comprises irradiating the surface of an intraocular lens with active light having emission peaks at a wavelength region of 185±5 nm and a wavelength region of 254±5 nm both at the same time that works to decompose oxygen molecules to generate ozone and that also works to decompose the ozone to generate active oxygen, in the presence of oxygen.

2. The process of claim 1, wherein the intraocular lens is a soft lens.

3. The process of claim 2, wherein the soft lens is formed of a soft acrylic material.

4. The process of claim 1, wherein the intraocular lens has an optic portion formed of a hard lens.

* * * * *